United States Patent
Schrenk et al.

(12) 
(10) Patent No.: US 6,324,897 B1
(45) Date of Patent: Dec. 4, 2001

(54) PARTIAL-PRESSURE SENSOR

(75) Inventors: Manfred Schrenk, VS-Schwenningen; Peter Weissbrodt, Jena; Erich Hacker, Jena; Dirk Mademann, Jena, all of (DE)

(73) Assignee: Jenoptik Aktiengesellschaft, Jena (DE)

( * ) Notice: Subject to any disclaimer, the term of this patent is extended or adjusted under 35 U.S.C. 154(b) by 0 days.

(21) Appl. No.: 09/686,118

(22) Filed: Oct. 11, 2000

Related U.S. Application Data

(63) Continuation-in-part of application No. 09/178,360, filed on Oct. 23, 1998.

(30) Foreign Application Priority Data

Oct. 27, 1997 (DE) .................................... 197 47 343

(51) Int. Cl.$^7$ ............................. G01N 7/00; G01N 21/00; G01L 7/00
(52) U.S. Cl. ...................... 73/31.05; 73/700; 422/83
(58) Field of Search ................................ 73/31.05, 29.01, 73/700, 705; 338/36; 385/124; 422/83; 436/134, 138

(56) References Cited

U.S. PATENT DOCUMENTS

| | | | |
|---|---|---|---|
| 4,668,635 | * 5/1987 | Forster | 436/134 |
| 4,764,343 | * 8/1988 | Nyberg | 422/83 |
| 4,926,156 | * 5/1990 | Dickert et al. | 338/36 |
| 4,982,598 | * 1/1991 | Dickert et al. | 73/29.01 |
| 5,173,432 | * 12/1992 | Lefkowitz et al. | 436/138 |
| 5,235,659 | * 8/1993 | Atkins et al. | 385/124 |

* cited by examiner

Primary Examiner—Hezron Williams
Assistant Examiner—Jay L. Politzer
(74) Attorney, Agent, or Firm—Reed Smith LLP

(57) ABSTRACT

A partial pressure sensor is disclosed which is suitable for determining the partial pressure of a gas or vapor in a thermally uncontrolled gas atmosphere over a large measurement range and with high measuring accuracy.

11 Claims, 1 Drawing Sheet

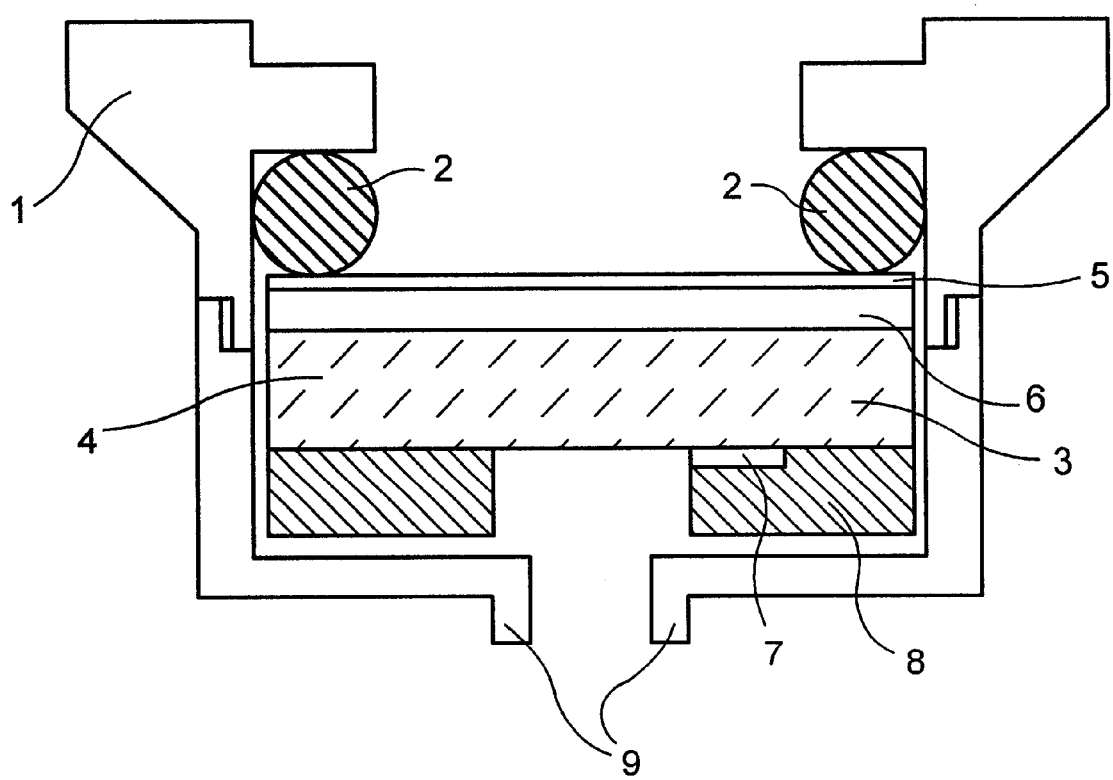
F I G. 1

PARTIAL-PRESSURE SENSOR

This is a continuation-in-part of application Ser. No. 09/178,360, filed Oct. 23, 1998, claiming priority to German Application 197 47 343.1 filed Oct. 27, 1997.

BACKGROUND OF THE INVENTION a) Field of the Invention

Gas molecules from a gas atmosphere formed of one or more gases or vapors can be absorbed by or given off into the gas atmosphere by optical coating systems. An absorption/emission equilibrium takes place depending on the pressure of the gas or the partial pressures of the gases. The varying degrees to which the different gases are absorbed and the influence of the gases on the optical characteristics of the coating system make it possible to deduce the partial pressure of an individual gas component.

b) Description of the Related Art

Most optical sensors based on this principle detect the change in intensity of the radiation reflected by or transmitted through this coating system as a measured quantity.

It has long been known, particularly for measurement of moisture, that optical coating systems formed of one or more dielectric single layers whose thickness is approximately equal to one fourth or one half of the wavelength of the measurement light are porous and change their reflection characteristics and transmission characteristics as a result of water absorption when there is a change in the moisture content of the surrounding air (see, e.g., Koch, "Optical Untersuchungen zur Wasserdampfsorption in Aufdampfschichten [Optical Investigations in Water Vapor Absorption in Evaporation Coatings]", phys. stat. sol., 12 (1965), pages 533–543).

DE 36 19 017 A1 proposes an optically dielectric moisture measurement device in which the optical coating system is arranged on a translucent carrier. The partially transmitting mirror formed in this way is placed in an optical beam path and a moisture-dependent measurement signal is formed by taking the quotient of the reflected and transmitted light intensities changing as a function of the absorption of moisture. The measurement signal formed in this way enables a highly sensitive detection of the change in the reflection behavior and transmission behavior of the optical coating system.

In all of the described solutions, a defined relationship is assumed between determined optical characteristics of the influenced optical coating system and diverse physical and chemical parameters of the medium acting on the coating system which allows a unique correlation between the measurement signal and the quantity of the parameter. Specifically, the partial pressure, especially the partial pressure of water vapor, is indicated as a parameter which can be determined.

The unique correlation of a measurement signal with a determined magnitude of partial pressure, especially partial pressure of water vapor, is sometimes highly prone to error.

The possibility of enabling measurements over a wide range of partial pressures of water vapor, especially in the low-moisture range, by means of defined optical coating systems lends increased significance to optical moisture sensors, e.g., for high-vacuum evaporation systems. The size of the moisture sensor is of secondary importance for the above-mentioned applications and, in addition, vacuum-tight fiber vias or lead-throughs are relatively expensive and are not available for ultra-high vacuum applications.

Therefore, it is impossible to arrange the coating system directly on a fiber surface (DE 3832185 C2). Gluing the substrate to the end face of the fiber (DE 4133126 A1) is relatively complicated and makes exchange impossible for further cases of application and/or as a consequence of aging processes.

The sensor material of the present invention composes an oxidic or fluoridic function coating in which steam or another gas (or other "steams" such as alcohol vapor) which is condensable at low temperatures is included. The water inclusion is based on adsorption and is therefore reversible without any external action when the partial pressure of the steam decreases. The sensor material does not change.

The sensor of the present invention makes use of the change in the refractive index due to the included gas or vapor for detection. The sensor coat is applied as an interference layer. The reflection effect relies on interference; therefore, the reflection is highly wavelength-dependent (reflection minima, reflection maxima). A change in the index of refraction of the sensor coat causes a spectral displacement of the reflection and transmission extrema of the arrangement. The emission of gas is carried out when the partial pressure of the gas falls. Therefore, no heating or temperature monitoring is required for the operation of the sensor in a gas atmosphere with constant temperature.

The measurement of reflection and light attenuation described in U.S. Pat. Nos. 4,764,343 and 4,668,635 is based on the metallic characteristic of the sensor material which is lost when combined with gas. At a given partial pressure, there is a determined temperature at which the conversion of metal to the metal compound, and vice versa, takes place. The detection of partial pressure is carried out ultimately by measurement of the conversion temperature. The very high temperatures are therefore necessary for the operation of the sensor.

The sensor coating of our sensor is a component part of an interference layer arrangement. The special arrangement of the interference layers brings about an improved readout and increased detection speed.

The tempering possibility in our sensor improves the measurement precision in the measurement of systems with inhomogeneous temperatures or temperatures which change over time.

The capability of the function coating of absorbing gas molecules can be limited through contact with liquids or gases. In this case, reduced measuring sensitivity must be expected in spite of recalibration. The arrangements make it possible to simply replace the sensor. For measurements particularly in ultra high-vacuum systems or in clean gas systems, adhesive compounds are undesirable because gas evolution of the adhesive impairs the function of the system. The arrangement of the sensor ensures an inexpensive and adhesive-free sealing and flanging to the system.

OBJECT AND SUMMARY OF THE INVENTION

The primary object of the invention is to provide a pressure-tight partial pressure sensor which is suitable for determining the partial pressure of a gas or vapor in a thermally uncontrolled gas atmosphere over a large measurement range and with high measuring accuracy.

This object is met in a partial pressure sensor comprising a measurement head and light-conducting fibers connected therewith in that the measurement head can be coupled with or uncoupled from the light-conducting fibers by means of a fiber connection flange, in that the measurement head has a housing in which a sensor is fastened in a pressure-tight manner, in that the sensor comprises a substrate with an optical coating system, and, further, a temperature gauge and a temperature-regulation element are arranged so as to communicate with the substrate. The optical coating system can comprise a reflection system and a function coating arranged above the latter. It may prove advantageous to arrange the temperature-regulation element and/or the temperature gauge so as to be integrated in the optical coating system.

The invention will be described more fully hereinafter with reference to an embodiment example.

BRIEF DESCRIPTION OF THE DRAWINGS

The embodiment example relates to a partial pressure sensor for measuring the partial pressure of water vapor in high-vacuum evaporation systems which is shown in FIG. 1.

DESCRIPTION OF THE PREFERRED EMBODIMENTS

The actual sensor 3 is arranged in a housing 1 so as to be sealed against the gas atmosphere via a high-vacuum seal 2 with a fiber connection flange 9 and a standard vacuum connection, not shown, which is located opposite to the latter and which produces a connection to the high-vacuum evaporation system that can be disconnected at any time. The sensor 3 comprises a transparent substrate disk 4 which has a reflection system 6 on one side and a function coating 5 above the latter, wherein the function coating 5 is in contact with the gas atmosphere.

The housing is detachably arranged at the high-vacuum system and, graphically expressed, the gas atmosphere of the high-vacuum system is represented by reference number 2 in FIG. 1. The high-vacuum seal 2 is arranged as shown in FIG. 1 so that no exchange or transfer can take place between the gas atmospheres (the gas atmosphere inside the high-vacuum evaporation system and that outside of the latter).

As its name suggests, the fiber connection flange 8 is present so that a light-conducting fiber cable can be arranged so as to be exchangeable with its end face at the substrate disk 3.

Consequently, the coating 4 constantly communicates with the gas atmosphere prevailing inside the high-vacuum system and there is no need for any additional features or any features not indicated in order to introduce the gas atmosphere or partial pressure to be determined in the high-vacuum system.

The sensor material of the present invention comprises an oxidic or fluoridic function coating in which steam or some other gas which is condensable at low temperatures (other "steams" such as alcohol vapor) in included. The water inclusion is based on adsorption and is therefore reversible without any external action when the partial pressure of the steam decreases. The sensor material does not change in the present invention. However, the art describes partial pressure sensors in which the sensor material is formed of a reactive material (metal, etc.) which enters into a chemical bond with the gas to be detected. In the present sensor, the change in the refractive index due to the included gas or vapor is used for detection. The sensor coat is applied as an interference layer. The reflection effect relies on interference; therefore, the reflection is highly wavelength-dependent (reflection minima, reflection maxima). A change in the index of refraction of the sensor coat causes a spectral displacement of the reflection and transmission extrema of the arrangement. The emission of gas is carried out when the partial pressure of the gas falls. Therefore, no heating or temperature monitoring is required for the operation of the sensor in a gas atmosphere with constant temperature.

The measurement of reflection and light attenuation described in the art is based on the metallic characteristic of the sensor material which is lost when combined with gas. At a given partial pressure, there is a determined temperature during the conversion of metal to the metal compound, and vice versa. The detection of partial pressure is carried out ultimately by the measurement of the conversion temperature. The very high temperatures are therefore necessary for the operation of the sensor.

Materials of the substrate disk 4 may be the same sorts of glass as usually used for optical filters. To ensure mechanical stability, the pressure range of the sensor and the ratio between thickness and diameter has to be considered, e.g., 2 mm thickness for a 20 mm diameter substrate disk 4 is good.

The reflection system 6 can be made, e.g., from an alternating coating of two dielectric materials made of silicon dioxide or silicon nitride as usually used in dielectric Fabry-Perot filters.

The quality of the vacuum in a high-vacuum evaporation system determines the quality of the coatings produced in the high-vacuum evaporation system. With a conventional pressure gauge only the total pressure can be monitored. To distinguish between a leakage from the water cooled evaporation sources and the sealing to the outer atmosphere a partial pressure sensor is necessary. Other applications for the sensor could be systems for high purer gases. A (small) leakage leads not necessarily to decreases of the total pressure, but it will change the partial pressures of the different components, e.g., water.

The reflection system 6 has the lowest possible absorption capacity or permeability with respect to moisture and changes its optical characteristics as little as possible as a function of the partial pressure of water vapor.

On the other hand, the optical characteristics in the function coating 5 which are used for detecting the partial pressure of water vapor change to the greatest degree possible as a function of the partial pressure of water vapor in the gas atmosphere. The function coating 5 and the reflection system 6 are adapted to one another in such a way that a simple optical evaluation is possible by means of measuring a sharp transmission extremum or reflection extremum. Since the water vapor chiefly interacts with the function coating 5, this arrangement achieves an improved reaction in the case of rapid changes in the partial pressure of water vapor.

The uncoated side of the substrate disk 4 directly contacts a temperature-regulation element 8, wherein a temperature gauge 7 is inserted therebetween in order to detect the temperature of the function coating 5 continuously with the least possible time delay during measurements. The function coating 5 can be heated or cooled to a determined temperature via the substrate disk 4 and the reflection system 6 by means of the temperature-regulation element 8. The partial pressure measurement range can be deliberately shifted by adjusting a determined constant temperature during the measuring operation. Condensation, e.g., during ventilation, can be prevented by adjusting a higher temperature than that of the evaporation system.

The glass fibers for illumination and readout can be connected with the housing 1 via a fiber connection flange 9 so as to be detachable. Therefore, one device is sufficient for optical readout for the readout of a plurality of partial pressure sensors (one after the other). It is mentioned that the high-vacuum seal 2 can be dispensed with insofar as the sensor 3 is enclosed in the housing 1 in such a way that no pressure compensation can take place.

While the foregoing description and drawings represent the preferred embodiments of the present invention, it will be obvious to those skilled in the art that various changes and modifications may be made therein without departing from the true spirit and scope of the present invention.

What is claimed is:

1. A partial pressure sensor comprises:

a measurement head;

light-conducting fibers being connected with said measuring head;

a fiber connection flange for coupling said light-conducting fibers with or uncoupling said light conducting fibers from said measurement head;

said measurement head having a housing in which a sensor is fastened in a pressure-tight manner;

said sensor comprising a substrate provided with an optical coating system;

and a temperature-regulation element and a temperature gauge which communicates with said substrate;

and wherein said sensor functions by absorption of gas in said gas atmosphere which changes the index of refraction of said sensor coating and wherein said absorption of gas by said sensor coating is reversible resulting in no chemically reactive degradation of said sensor coating.

2. The partial pressure sensor according to claim 1, wherein said optical coating system comprises a reflection system and wherein a function coating is arranged above said reflection system.

3. The partial pressure sensor according to claim 1, wherein said temperature gauge is arranged between said substrate and said temperature regulation element.

4. The partial pressure sensor according to claim 1, wherein said temperature gauge and said temperature-regulation element are integral component parts of said optical coating system.

5. An optical partial pressure sensor for use with vacuum systems comprising:

a housing engageable with said vacuum system;

a vacuum seal within said housing for separating said vacuum system from a gas atmosphere located adjacent to a sensor coating for detecting gas pressure;

a reflection system located adjacent to said sensor coating;

a transparent substrate sensor disk located adjacent to said reflection system;

and a filter connection flange located adjacent to said substrate sensor disk;

and wherein said sensor functions by absorption of gas in said gas atmosphere which changes the index of refraction of said sensor coating and wherein said absorption of gas by said sensor coating is reversible resulting in no chemically reactive degradation of said sensor coating.

6. The optical partial pressure sensor of claim 5 further comprising:

a temperature gauge for detecting temperature of said sensor coating.

7. The optical partial pressure sensor of claim 6 further comprising:

a temperature regulating element for regulating said temperature of said sensor coating.

8. The optical partial pressure sensor of claim 5 wherein said transparent substrate sensor disk is made of glass.

9. The optical partial pressure sensor of claim 5 wherein said absorption of gas includes an absorption of water vapor.

10. The optical partial pressure sensor of claim 5 wherein said absorption of gas includes absorption of alcohol vapor.

11. The optical partial pressure sensor of claim 5 wherein said vacuum system is separated from said gas atmosphere using a vacuum seal rather than a physical member.

* * * * *